United States Patent [19]

Howson

[11] Patent Number: 5,047,418

[45] Date of Patent: Sep. 10, 1991

[54] METHOD OF STIMULATING HISTAMINE $H_3$-RECEPTORS

[75] Inventor: William Howson, Welwyn, United Kingdom

[73] Assignee: Smith Kline & French Laboratories Limited, Welwyn Garden City, England

[21] Appl. No.: 556,921

[22] Filed: Jul. 20, 1990

[30] Foreign Application Priority Data

Jul. 25, 1989 [GB] United Kingdom ............... 8916947

[51] Int. Cl.$^5$ .................. A61K 31/415; A61K 9/70
[52] U.S. Cl. ............................. 514/400; 514/824; 426/449; 426/456; 426/434; 426/435
[58] Field of Search .......................... 514/400, 826

[56] References Cited

U.S. PATENT DOCUMENTS

| | | | |
|---|---|---|---|
| 3,759,944 | 9/1973 | Black et al. | 260/309 |
| 3,891,764 | 6/1975 | Black et al. | 424/273 |
| 3,894,151 | 7/1975 | Black et al. | 424/246 |
| 3,954,982 | 5/1976 | Black et al. | 424/246 |
| 4,000,302 | 12/1976 | Black et al. | 424/273 |

OTHER PUBLICATIONS

Sterk et al., Arch. Pharm. 319(7), 624–630 (1986).
Sterk et al., Agents and Actions, 18, (1–2), 137–140 (1986).
Impicciatore et al., Il Farmaco. Ed. Sci., 35 (5), 418–424 (1980).

Primary Examiner—Thurman K. Page
Assistant Examiner—G. S. Kishore
Attorney, Agent, or Firm—Linda E. Hall; Stuart R. Suter; Edward T. Lentz

[57] ABSTRACT

A pharmaceutical composition is described which comprises a pharmaceutically acceptable carrier and a compound of the formula (1):

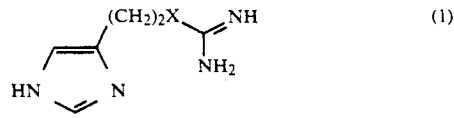

or a pharmaceutically acceptable salt thereof wherein X is $CH_2$ or S, in an amount sufficient to stimulate selectively histamine $H_3$-receptors.

2 Claims, No Drawings

METHOD OF STIMULATING HISTAMINE H₃-RECEPTORS

The present invention relates to pharmaceutical compositions comprising imidazole derivatives and a method of stimulating histamine H₃-receptors by administering them.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by $H_1$-antagonists such as mepyramine. A second type of receptor is known as the histamine $H_2$-receptor (Black et al., Nature 1972, 236, 385) which is not blocked by mepyramine but by $H_2$-antagonists such as burimamide or cimetidine. A third type of receptor known as the histamine $H_3$-receptor has more recently been identified (e.g. Arrang et al., Nature 1987, 327, 117 and Van der Werf et al., (1989) Trends Pharmacol. Sci. 10, 159) which is stimulated by $H_3$-agonists such as (R)-α-methylhistamine and blocked by $H_3$-antagonists such as thioperamide.

U.S. application No. 3759944 discloses isothiourea derivatives which are described as acting at histamine receptors other than the $H_1$-receptor and are of utility in inhibiting certain actions of histamine which are not inhibited by $H_1$-antagonists. A particular isothiourea described is S-[2-(4(5)-imidazolyl)ethyl]isothiourea dihydrobromide or dihydrochloride. This compound is also disclosed in U.S. application No. 3954982 wherein it is described as an $H_2$-antagonist. The prime utility of an $H_2$-antagonist would be in the treatment of duodenal, gastric, recurrent and stomal ulceration and reflux oesophagitis.

U.S. application No. 3891764 discloses amidine derivatives as histamine $H_2$-antagonists. A particular compound described is 4-(4(5)-imidazolyl)butyramidine dihydrochloride.

It has now been discovered that the above named imidazole compounds are highly potent selective histamine $H_3$-agonists.

Accordingly the present invention provides a pharmaceutical composition comprising a pharmaceutically acceptable carrier and a compound of the formula (1):

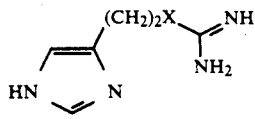

(1)

or a pharmaceutically acceptable salt thereof:
wherein X is CH₂ or S,
in an amount sufficient to stimulate selectively histamine H₃-receptors.

In a further aspect this invention provides a method of stimulating histamine H₃-receptors in a host in need thereof which comprises administering an effective amount to stimulate said receptors of a compound of formula (1) or a pharmaceutically acceptable salt thereof.

Particular compounds of the formula (1) are: S-[2-(4(5)-imidazolyl)ethyl]isothiourea or
4-(4(5)-imidazolyl)butyramidine
or pharmaceutically acceptable salts thereof.

These compounds can form pharmaceutically acceptable acid addition salts with hydrochloric, hydrobromic, sulphuric, phosphoric, acetic, citric, maleic, lactic, ascorbic, fumaric, oxalic, methanesulphonic and ethanesulphonic acids.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts can be administered in standard manner for example orally, sublingually, parenterally, transdermally, rectally, via inhalation or via buccal administration.

Compounds of formula (1) and their pharmaceutically acceptable salts which are active when given orally or via buccal administration can be formulated appropriately in dosage forms such as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations can be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions can be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene glycol, polyvinylpyrrolidone, 2-pyrrolidone, cyclodextrin, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.1 mg to 50 mg, and preferably from 1 mg to 25 mg, and each dosage unit for parenteral administration contains suitably from 0.1 mg to 25 mg, of a compound of formula (1) or a pharmaceutically acceptable salt thereof calculated as the free base.

The daily dosage regimen for oral administration is suitably about 0.1 mg to 200 mg, preferably 1 mg to 100 mg, of a compound of formula (1) or a pharmaceutically acceptable salt thereof calculated as the free base. The daily dosage regimen for parenteral administration is suitably about 0.1 mg to 100 mg, for example about 1 mg to 40 mg, of a compound of the formula (1) or a pharmaceutically acceptable salt thereof calculated as the free base. The active ingredient may be administered as required for example from 1 to 4 times a day or by infusion. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are $H_1$-antagonists such as mepyramine, $H_2$-antagonists such as cimetidine or ranitidine, phosphodiesterase inhibitors such as theophylline or aminophylline, bronchodilators such as sympathomimetic amines for example isoprenaline, isoetharine, salbutamol, phenylephrine or ephridine or anti-allergic agents such as disodium cromoglycate.

The histamine $H_3$-agonist activity of the compounds of formula (1) was assessed by a method similar to that described by Trzeciakowski (1987), J. Pharmacol. Exp. Ther., 243, 874–880. Inhibition of the electrically evoked twitch responses of the guinea-pig ileum by histamine $H_3$-receptor agonists was studied by addition of graded concentrations of the compound (in volumes of 25 μl or 79 μl) to the organ bath in a sequential manner. Each concentration of agonist was washed out of the bath when the response had reached equilibrium. A four minute period was allowed between each addition of the compound. The concentration of compound which caused 50% inhibition of the twitch response is given as the $EC_{50}$ (nM). The following results were obtained:

| Compound of formula (1) | $EC_{50}$ (nM) |
| --- | --- |
| X = S | 4.6 |
| X = $CH_2$ | 1.1 |
| (R)-α-methylhistamine | 60 |

The activity of the compounds of the formula (1) at the histamine $H_1$- or $H_2$-receptor was assessed substantially as described by Parsons et al., Agents and Actions, 1976, 7(1), 31. On the guinea-pig atrium the compound of the formula (1) wherein X is S demonstrated histamine $H_2$-agonist activity in the range $5 \times 10^{-5}$M to $10^{-4}$M whilst the corresponding compound where X is $CH_2$ had no histamine $H_2$-agonist activity up to $10^{-5}$M.

Results obtained on the guinea-pig atrium demonstrate weak histamine $H_2$-antagonist activity:

| Compound of formula (1) | pA$_2$ |
| --- | --- |
| X = S | 4.1 |
| X = $CH_2$ | ca 3.6 |

On the guinea-pig ileum the compound of the formula wherein X is S demonstrated histamine $H_1$-agonist activity in the range $10^{-4}$ to $10^{-3}$M, whilst the corresponding compound where X is $CH_2$ had no histamine $H_1$-agonist activity up to $10^{-5}$M.

On the guinea-pig ileum the compound of the formula (1) wherein X is $CH_2$ had no histamine $H_1$-antagonist activity up to $10^{-5}$M.

The above results indicate that the compounds of the formula (1) are highly potent selective histamine $H_3$-agonists, being about 10000 times more potent at the histamine $H_3$-receptor than at either the histamine $H_1$- or $H_2$-receptor.

Agonists of the histamine $H_3$-receptor are believed to inhibit the synthesis and release of neurotransmitters such as histamine and are therefore likely to decrease neurotransmitter release in the digestive tract and in the nervous, cardiovascular and immune systems. They are likely to have utility as a sedative, as a sleep regulator, anti-convulsant, regulator of hypothalamohypophyseal secretion, anti-depressant and modulator of cerebral circulation. Modification of release of the messengers of immune responses is likely to modulate the immune system.

It is believed that the compounds of the formula (1) will be particularly useful in the treatment of allergic diseases such as allergic asthma, allergic rhinitis or urticaria or in the treatment of gastrointestinal motility disorders such as irritable bowel syndrome. The use of histamine $H_1$- or $H_2$-antagonists alone or in combination is not regarded as being efficacious. Histamine $H_1$ or $H_2$-agonists would be contra-indicated for such disease states.

The following example serves to illustrate a pharmaceutical composition of this invention.

EXAMPLE 1

A pharmaceutical composition for oral administration is prepared containing:

| | % by weight |
| --- | --- |
| A | |
| 4-(4-(5)-imidazolyl)butyramidine | 55 |
| Dibasic calcium phosphate dihydrate | 20 |
| Approved colouring agent | 0.5 |
| Polyvinylpyrrolidone | 4.0 |
| B | |
| Microcrystalline Cellulose | 8.0 |
| Maize Starch | 8.0 |
| Sodium glycollate | 4.0 |
| Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 10 mg, 25 mg or 50 mg of the free base.

What is claimed is:

1. A method of stimulating histamine $H_3$-receptors in a patient in need thereof which comprises administering a patient an effective amount to stimulate said receptors of a compound of the formula (1):

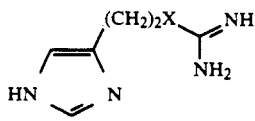 (1)

or a pharmaceutically acceptable salt thereof
wherein X is $CH_2$ or S.

2. A method of treating gastrointestinal motility disorders in a host in need thereof which comprises administering an effective amount for said treatment of a compound of the formula (1):

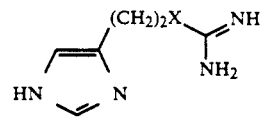 (1)

or a pharmaceutically acceptable salt thereof
wherein X is $CH_2$ or S.

* * * * *